United States Patent [19]
Faulkner et al.

[11] Patent Number: 5,624,554
[45] Date of Patent: Apr. 29, 1997

[54] COLLECTION AND TRANSFER DEVICE

[75] Inventors: Michael Faulkner; John E. Fay, both of Leominster, Mass.

[73] Assignee: Biomedical Polymers, Inc., Leominster, Mass.

[21] Appl. No.: 363,630

[22] Filed: Dec. 23, 1994

Related U.S. Application Data

[63] Continuation-in-part of Ser. No. 156,286, Nov. 22, 1993, abandoned.

[51] Int. Cl.[6] .................. B01D 35/02; G01N 1/08; G01N 33/483; C12M 1/12
[52] U.S. Cl. .................. 210/232; 210/238; 210/464; 210/466; 210/469; 210/474; 210/482; 422/101; 422/102; 435/307.1; 435/283.1; 436/177; 436/178; 222/189.06; 73/863.23; 73/863.25; 73/864.44; 73/864.91
[58] Field of Search ...................... 210/232, 238, 210/445, 446, 464, 465, 466, 467, 468, 469, 474, 482; 422/101, 102; 435/311; 436/177, 178; 222/189; 141/286; 73/863.23, 863.24, 863.25, 864.44, 864.91

[56] References Cited

U.S. PATENT DOCUMENTS

| | | |
|---|---|---|
| 4,225,423 | 9/1980 | Cotey . |
| 4,559,837 | 12/1985 | Cerqueira . |
| 4,859,610 | 8/1989 | Maggio . |
| 5,149,506 | 9/1992 | Skiba . |
| 5,198,365 | 3/1993 | Grow . |
| 5,431,884 | 7/1995 | McDonough . |
| 5,440,942 | 8/1995 | Hubbard . |

*Primary Examiner*—Thomas M. Lithgow
*Attorney, Agent, or Firm*—Iandiorio & Teska

[57] ABSTRACT

A collection and transfer device including a collection vessel having an opening on one end and a closure apparatus engageable therewith which has a collection device receivable within the collection vessel, and a passage therethrough for transferring a collected sample from within the collection vessel to a centrifuge or other type of vessel or microscope slide.

4 Claims, 4 Drawing Sheets

COLLECTION AND TRANSFER DEVICE

RELATED INVENTIONS

This application is a continuation-in-part application of U.S. patent application Ser. No. 08/156,286, filed Nov. 22, 1993, (now abandoned) entitled "Filter and Transfer System".

FIELD OF INVENTION

This invention relates to an improved collection and transfer device for collecting, transferring, and filtering a medical sample.

BACKGROUND OF INVENTION

There are a number of applications, usually medical, in which solid particles are to be extracted from a liquid/solid slurry. The particles to be examined may be captured by a filter or may be passed by the filter while larger, undesired particles are blocked. One specific medical application includes the separation of parasite larvae and eggs from a stool sample placed in a specimen vial filled with a fixative or preservative. The devices used for this application are typically called "stool transportation and filtration systems". One improvement over previous devices is discussed in U.S. Pat. No. 4,675,110 assigned to the same entity as this application. In that device, one improvement involved the equalization of pressure between a collection vessel and an attached receptacle vessel.

There are some devices on the market for collecting and filtering such samples, but few offer a safe, closed system in which collection and transfer occurs without any chance of spillage. Some devices spill easily, others include filters susceptible to blockage. Still others require additional components in order to collect and agitate a sample or will only work properly with specially fabricated components. Most are difficult to use and may confuse the technician, or worse, the patient.

SUMMARY OF INVENTION

It is therefore an object of this invention to provide an improved collection and transfer device.

It is a further object of this invention to provide such an improved collection and transfer device which facilitates a closed system thus preventing samples from being exposed to the environment and reducing the chance of contamination of components and, more importantly, personnel during handling by the patient and the technician, during storage, transport, and filtering operations.

It is a further object of this invention to provide such an improved collection and transfer device which facilitates control of the filtering process and reduces the chance of overflow.

It is a further object of this invention to provide such an improved collection and transfer device which not only provides fairly precise control of the fluid flow through the filter but which also retains the remaining fluid after the flow has been stopped, thereby preventing dripping.

It is a further object of this invention to provide such an improved collection and transfer device which, if accidentally tipped over, will not spill.

It is a further object of this invention to provide such an improved collection and transfer device which is less prone to blockage as prior devices.

It is a further object of this invention to provide such an improved collection and transfer device which does not require the use of additional components in order to collect and agitate a sample.

It is a further object of this invention to provide such an improved collection and transfer device which works with and accommodates a number of different size receptacles and transfer vessels.

It is a further object of this invention to provide such an improved collection and transfer device which is simple to use and foolproof.

This invention results from the realization that effective and safe collection, preservation, transportation, and filtering of a medical sample can be accomplished if the collection vessel for the medical sample is made resiliently deformable so that it can be squeezed to transfer fluid from within the vessel and then released to not only stop the flow but to create a negative pressure with the vessel to retain the remaining fluid thus preventing leakage and dripping, and also that if the closure for the collection vessel is fabricated with an integral collection spoon/agitator device, a filter, and a transfer passage which is also sealable by means of a lockable cap, the result is a complete and foolproof collection/transfer kit. Another feature of this invention is a frangible seal for the transfer passage which makes the technician's job easier. Still another feature of this invention is a key for the lockable cap which is kept and used only by the technician thereby ensuring that the patient uses the collection vessel in the way intended.

This invention features and may suitably comprise, include, consist essentially of, or consist of a collection and transfer device. There is a collection vessel having an opening on one end and a closure apparatus engageable therewith. The closure apparatus includes a shank portion typically terminating in a collection device receivable within the collection vessel. The closure apparatus further includes a passage therethrough for transferring a sample from within the collection vessel.

The collection device may include a collection spoon, an agitator portion for mixing a sample within the collection vessel, and/or a fork portion. In a preferred embodiment the collection vessel includes a conical cavity for receiving the collection spoon.

The collection vessel typically has a threaded opening and the closure apparatus has a corresponding threaded portion for engaging the threaded opening of the collection vessel.

The collection vessel may be resiliently deformable for pressure feeding a sample therefrom through the passage. There is a filter portion in communication with the passage for filtering a sample as it passes through the passage. There is also a device for sealing the passage, such as a frangible sealing member and/or a cap sealingly engageable with the passage of the closure apparatus. A special key for removing the cap ensures that the device is used correctly by the patient.

The closure apparatus includes a portion for sealingly engaging a receptacle vessel therewith and may include a plurality of different size portions for sealingly engaging different size receptacle vessels therewith.

This invention also features a closure and filter apparatus for a sample collection vessel. The closure and filter apparatus includes a shank portion receivable within a collection vessel; a passage through the closure and filter apparatus for transferring a sample from within a collection vessel; and a filter in communication with the passage for filtering a sample as it passes through the passage. The shank portion terminates in a collection spoon which may include a vane portion for mixing a sample within the collection vessel, and/or a fork portion.

A device for sealing the passage, such as a frangible sealing member, and/or a cap sealingly engageable with the passage of the closure apparatus, ensures a closed system. There is a special key for removing the cap from the closure apparatus. For transfer, the closure and filter apparatus further includes a portion for sealingly engaging a receptacle vessel therewith or even a plurality of different diameter portions for sealingly engaging different size receptacle vessels therewith.

This invention also features a closure and filter apparatus for a collection vessel, the closure and filter apparatus comprising a collection device; a passage through the closure and filter apparatus for transferring a sample from within the collection vessel; a filter in communication with the passage for filtering a sample as it passes through the passage; and means for sealing the passage. The collection device may include an agitator portion for mixing a sample within a collection vessel, and/or a fork portion. The means for sealing the passage typically includes a frangible sealing member, and/or a cap sealingly engageable with the passage of the closure apparatus.

DISCLOSURE OF PREFERRED EMBODIMENT

Other objects, features and advantages will occur to those skilled in the art from the following description of a preferred embodiment and the accompanying drawings, in which.

Figure 1:
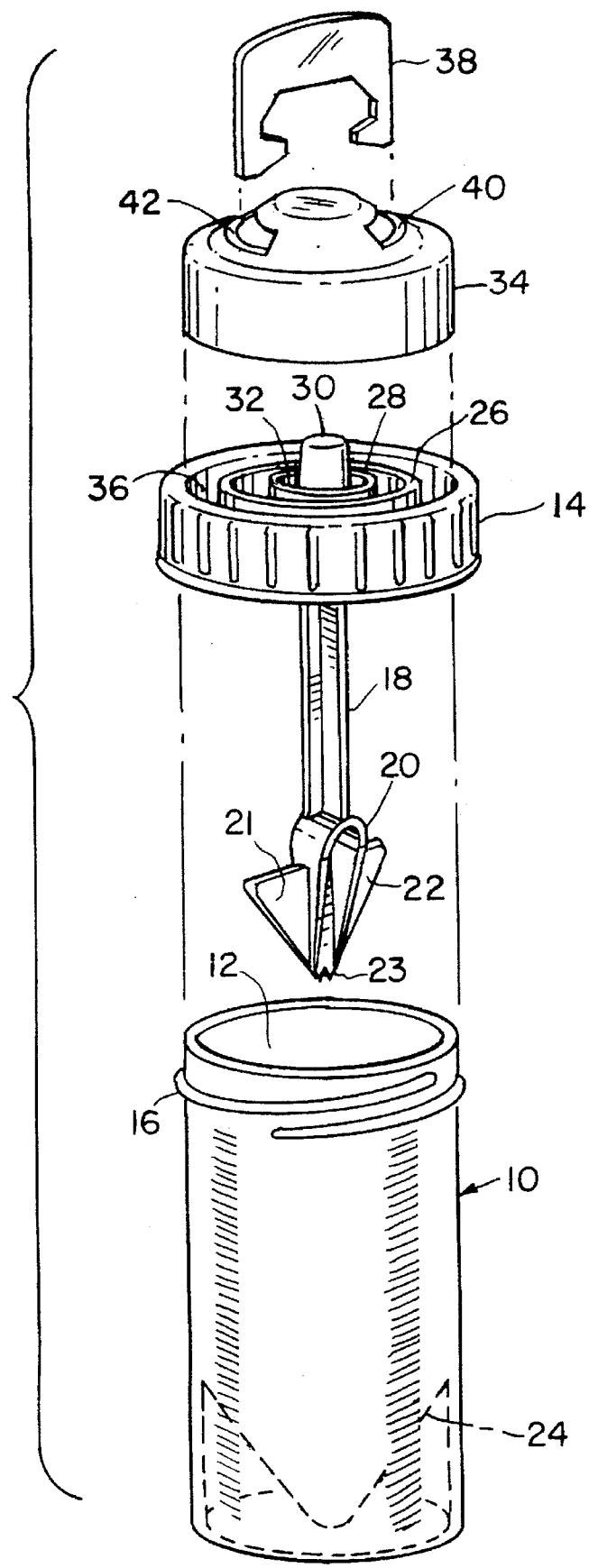
FIG. 1 is an exploded perspective view of the collection and transfer device of this invention.

This invention may be accomplished with a collection vessel 10, FIG. 1, having an opening 12 on the top end thereof. In a preferred embodiment, the collection vessel is resiliently compressible or deformable and made of a material such as polypropylene in the form of a 50 cc tube which can be squeezed temporarily to force out fluid within it and then released to resume its original form. Although low-density polyethylene could be used as the material or the collection vessel, polypropylene is preferred because of it superior chemical resistance properties.

The collection and transfer device of this invention also features closure apparatus 14 which engages threads 16 of collection vessel 10 or a bead or some other means by which closure apparatus 14 can be sealed with respect to collection vessel 10. Also, in a preferred embodiment, closure apparatus 14 includes shank portion 18 which is received within collection vessel 10. Shank 18 terminates in spoon portion 20 and also includes agitator vanes 21 and 22 for collecting a sample, placing it inside collection vessel 10, and then mixing it properly with a fixative or preservative within collection vessel 10. Other types of collective devices other than spoon 20 are within the scope of this invention. Collection vessel 10 includes conical cavity 24 for receiving collection spoon 20 and also providing an appropriate space for ensuring proper agitation by means of agitator vanes 21 and 22. Spoon portion 20 may include fork portion 23 to further facilitate collection of a sample.

Figure 3:
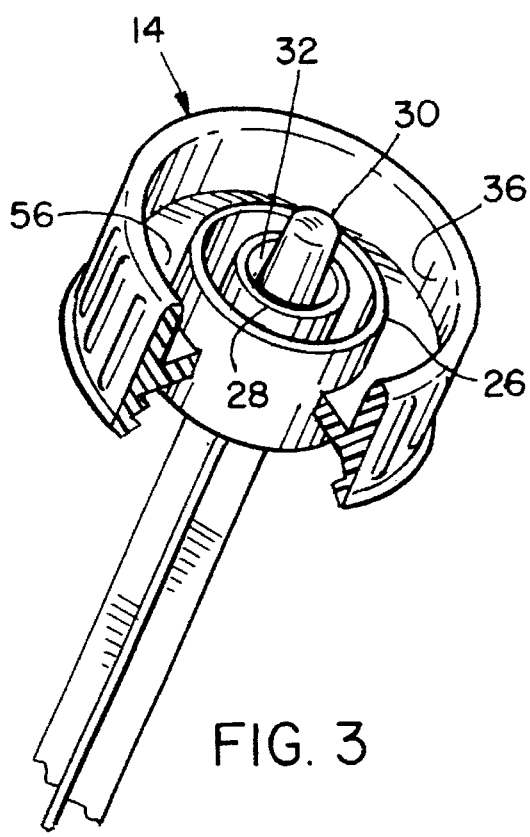
FIG. 3 is a perspective view of the top portion of the closure apparatus of this invention showing the frangible seal for the transfer passage.

Closure apparatus 14 includes one or more portions 26 and 28 for sealingly engaging a number of different sized receptacle or transfer vessels shown more clearly with respect to FIG. 3. Closure apparatus 14 also includes frangible sealing member 30 for temporarily sealing passage 32 through closure apparatus 14. Passage 32 allows transfer of a sample from within collection vessel 10 through closure apparatus 14 (once frangible sealing member 30 is broken) to a receptacle vessel (not shown), a microscope slide or the like.

Once frangible portion 30 is broken, locking cap 34 seals passage 32 in closure apparatus 14 during further transport or storage of the collection and transfer device. Cap 34 sealingly engages closure apparatus 14 by means of a press fit within the outside wall 36 of closure apparatus 14. Cap 34 is removed from closure apparatus 14 by means of key 38 which fits in slots 40 and 42 of cap 34. In this way, the patient is provided with the collection and transfer device of this invention with cap 34 in place within closure apparatus 14 and frangible sealing member 30 unbroken. That way, it is readily apparent to the patient that he must unscrew closure apparatus 14 and then use collection spoon 20 to place a stool sample within collection vessel 10. He then screws closure apparatus 14 back onto collection vessel 10 and hands the closed device to the technician or other medical personnel in possession of key 38. The technician then removes cap 34 and breaks frangible portion 30 to transfer fluid from within collection vessel 10 to a receptacle vessel for centrifuging or a microscopic slide for evaluation. In a preferred embodiment, collection vessel 10 is resiliently deformable and with cap 34 removed and frangible seal 30 broken, transfer passage 32 is open and any required amount of fluid can be squeezed out of collection vessel 10 and through the filter within the closure apparatus 14.

Figure 2:
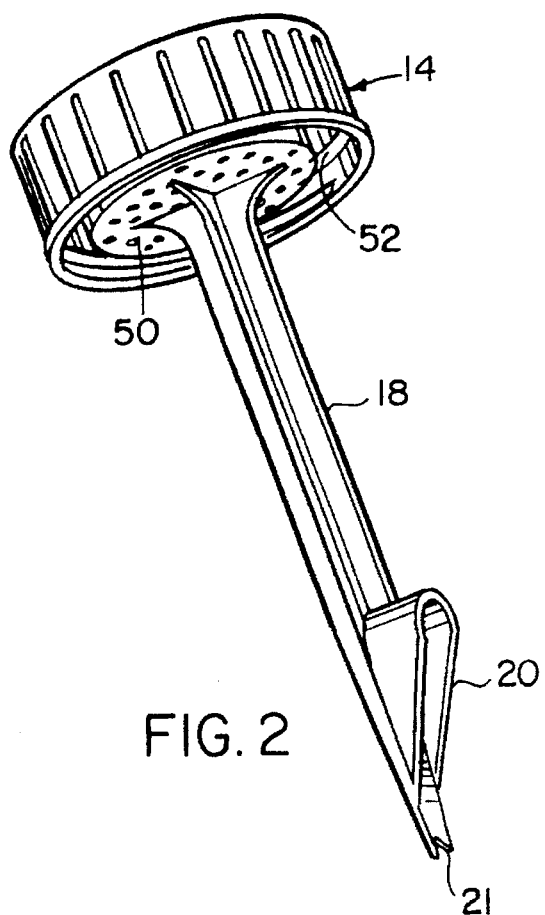
FIG. 2 is a perspective view of the closure apparatus of the subject invention showing the integral filter portion as well as the collection spoon.

As shown in FIG. 2, closure apparatus 14 typically includes integral filter portion 50. Also, as more clearly shown in FIG. 2, closure apparatus 14 includes internal threads 52 which mate with threads 16, FIG. 1, of collection vessel 10. Rim 54, FIG. 4, of sealing cap 34 fits snugly against wall 36, FIG. 3, of closure apparatus 14. Closure apparatus 14 includes cavity 56 which includes raised portions 26 and 28 for accepting different diameter receptacle, transfer or centrifuge vessels.

Figure 4:
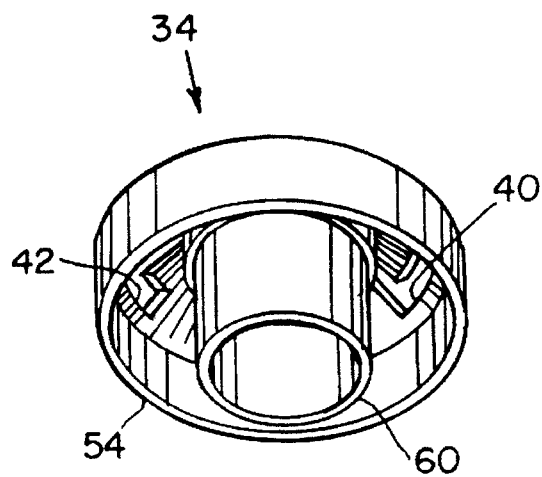
FIG. 4 is a perspective view of the sealing cap for sealing the transfer passage of the closure apparatus of this invention.

Cap 34, FIG. 4, includes outer wall 54 which is received within and about wall 36 of closure 14, FIG. 3. Portion 60 of cap 34, FIG. 4, fits snugly over passage 32, FIG. 3, but within the confines of raised portion 26 thereby effecting a seal of passage 32 after frangible seal portion 30 is broken. Frangible seal portion 30 is more clearly shown in FIG. 5. It includes twist-off handle portion 64 and thin plastic frangible portions 66 and 68 which temporarily seal passage 32 until handle portion 64 is torqued slightly by the technician.

Figure 6:
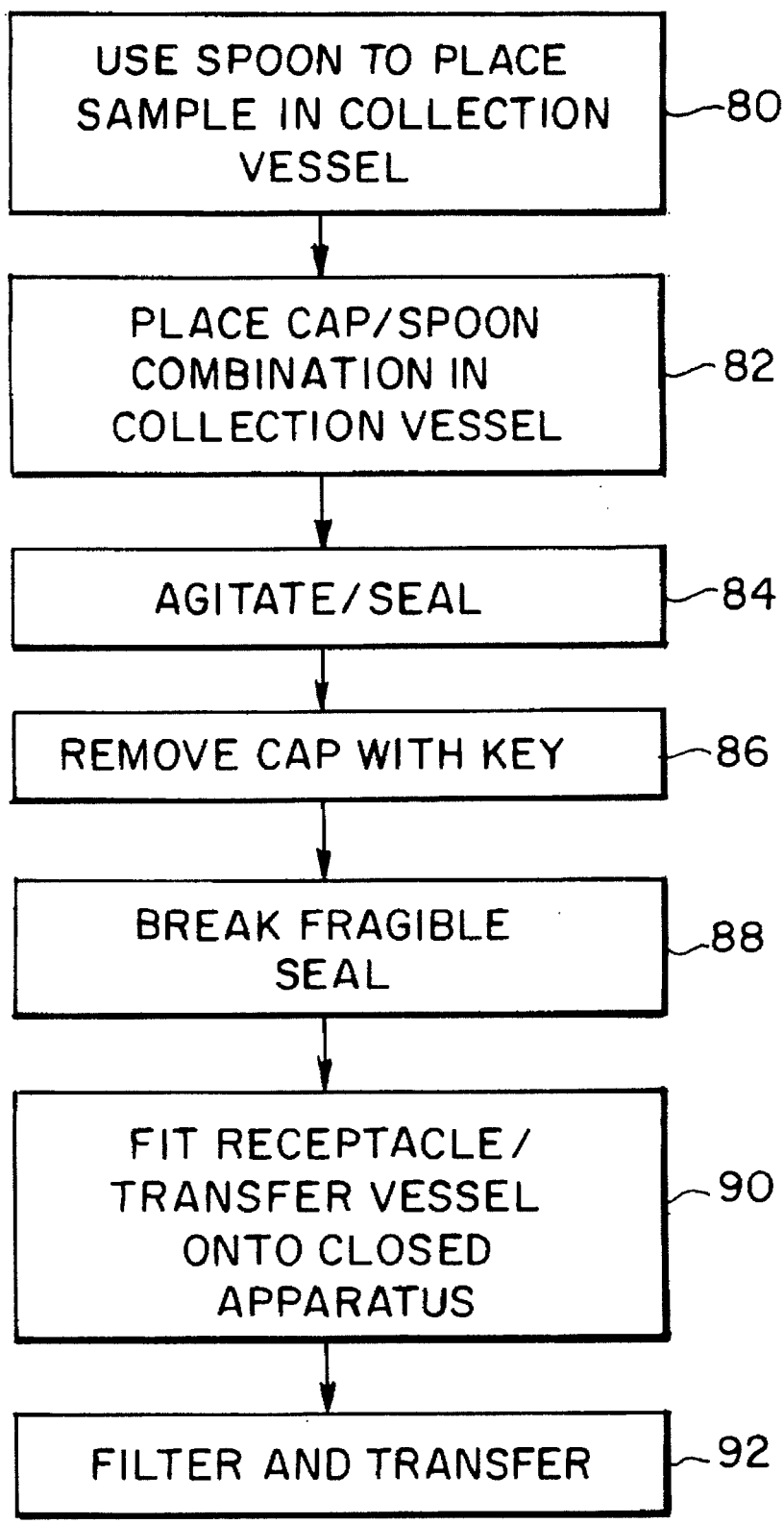
FIG. 6 is a flow chart depicting the intended method of use of the collection and transfer device of this invention.

In use, the device is filled with a fixative or preservative and is given to a patient without key 38, FIG. 1, for cap 34. The patient will then readily understand that closure apparatus 14 should be unscrewed and spoon 20 is to be used to place the sample in collection vessel 10, step 80, FIG. 6. After this is accomplished, the patient then re-seals collection vessel 10 by screwing the closure apparatus 14 back onto collection vessel 10, step 82. This sealed container is then handed to the technician who twists closure apparatus 14 to properly agitate the sample within collection vessel 10, step 84.

Figure 5:
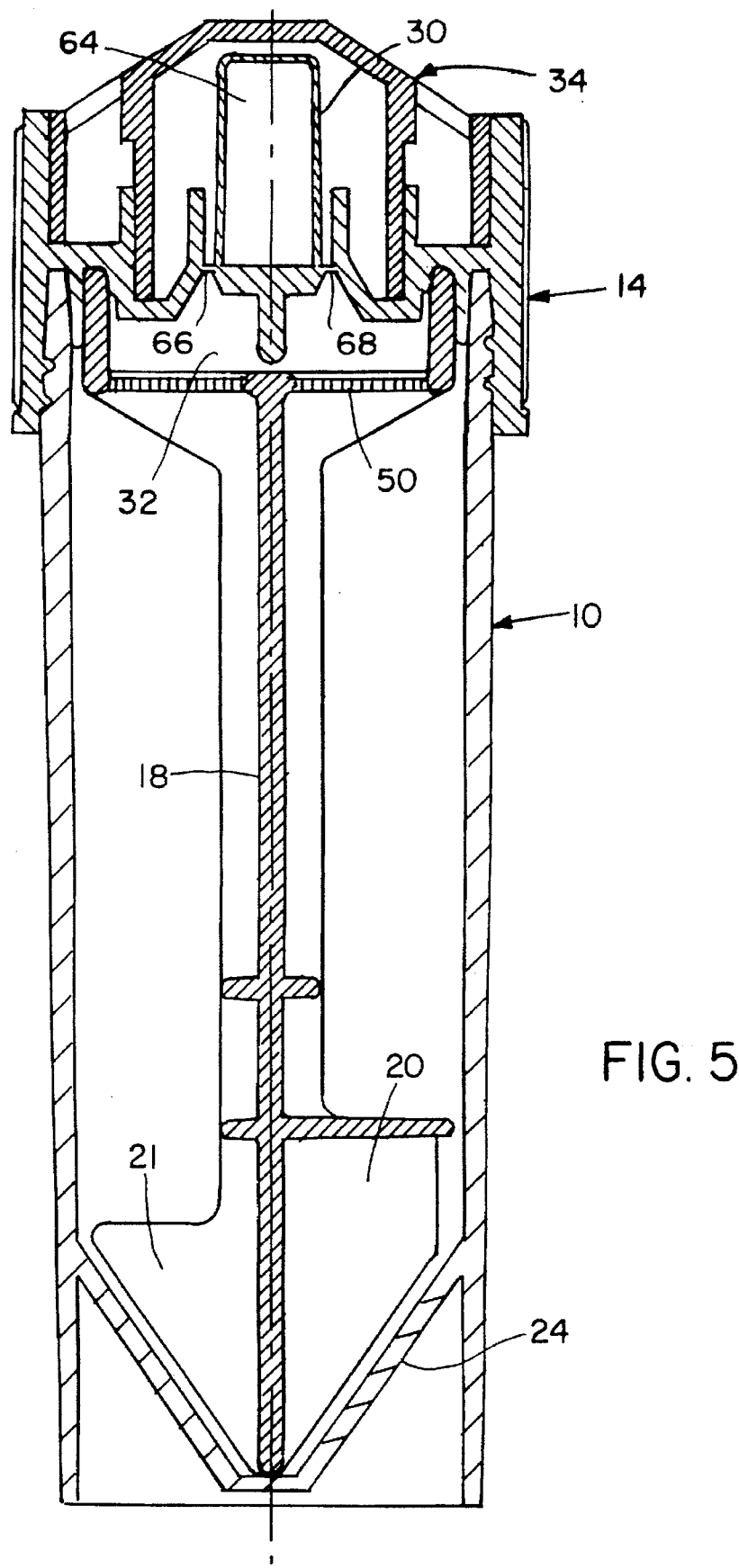
FIG. 5 is a side plan view of the collection and transfer device of this invention.

The closed, sealed device may then be safely stored or transported for laboratory analysis. For analysis or fluid transfer/filtering operations, key 38 is used to remove cap 34, step 86. Then, step 88, handle portion 64, FIG. 5, is twisted, torqued or pivoted slightly to break frangible portions 66 and 68 of frangible seal 30, FIG. 1. This opens transfer passage 32. A suitable transfer or receptacle vessel (not shown) may then be fitted about raised portions 28 or 26 (or within outer wall 36 of closure apparatus 14) providing a closed transfer system, step 90, as collection vessel 10 is squeezed and the appropriate contents within collection vessel 10 are filtered and passed through transfer passage 32, step 92.

Upon release of collection vessel 10 a vacuum will automatically retain any remaining fluid even when the collection vessel is inverted, preventing leaks and drips. For example, at the laboratory, the cap covering the closure apparatus is removed and the frangible seal is broken. A centrifuge tube is then mounted on one of the corresponding raised portions or nipples in a sealing engagement such as by a frictional or interference fit. The entire assembly is then inverted and the compressible collection vessel is squeezed to force fluid through the filter and the passage through the closure apparatus and into a centrifuge tube. When the lab technician sees that the right amount of specimen sample has been delivered to the receptacle vessel or centrifuge tube, he or she releases the collection vessel which thereupon returns to its normal shape and creates a small negative pressure that retains the remaining fluid in the inverted collection vessel preventing leaks and drips while the centrifuge tube is removed, the cap is placed on the closure apparatus and a corresponding cap is placed on the centrifuge tube.

In this way, the invention of this application provides a closed system preventing samples from being exposed to the environment and reducing the chance of contamination of components, the sample itself, and/or personnel. The compressible nature of the collection vessel of this invention facilitates control of the filtering process and reduces the chance of overflow. It provides a fairly precise flow of fluid through the filter but also retains any remaining fluid after the flow has been stopped, thereby preventing dripping.

This invention features a closed system which if accidentally tipped over or dropped will not spill. The filter and the integral nature of the filter within the closure apparatus provides a device which is not as prone to blockage as prior devices. No additional components are required to collect and agitate a sample. A collection device such as a collection spoon with an agitator portion and even a fork portion is provided as an integral part of the closure apparatus. Finally, this invention works with and accommodates a number of different sized receptacles such as centrifuge and transfer vessels and is simple to use and foolproof.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A collection and transfer device comprising:

a collection vessel having an opening on one end;

a closure apparatus engageable with said opening; said closure apparatus including a shank portion connected to said closure apparatus and receivable within said collection vessel, said closure apparatus further including a passage through said closure apparatus for transferring a sample from within said collection vessel to the exterior of said collection vessel;

a frangible sealing member for sealing said passage; and a cap sealingly engageable with said closure apparatus.

2. The collection and transfer device of claim 1 further including a key for removing said cap.

3. A collection and transfer device comprising:

a collection vessel having an opening on one end;

a closure apparatus engageable with said opening; said closure apparatus including a shank portion connected to said closure apparatus and the shank portion having agitator vanes receivable within said collection vessel;

said closure apparatus further including a passage therethrough for transferring a sample from within said collection vessel to the exterior of said collection vessel;

said collection vessel including a conical cavity for receiving the vanes of said shank portion;

said vanes being closely spaced from the walls of said conical cavity to enable proper agitation of a sample;

said device further including a cap sealable with respect to said closure apparatus and a frangible sealing member for sealing said passage through said closure apparatus.

4. A collection vessel and transfer device comprising:

a collection vessel having an opening on one end;

a first cap sealingly engaged with said open end of said collection vessel, the first cap including:

a shaft connected on one end thereof to said first cap, said shaft terminating in a device including a fork portion, a spoon portion, and at least one agitator vane;

said first cap further including a passage therethrough for transferring material form said collection to the exterior thereof, said first cap further including a filter in communication with said passage for filtering material transferred out of said collection vessel;

said first cap further including a rim for sealingly engaging a transfer vessel;

said collection vessel and transfer device further including a second cap sealingly engageable with said first cap; and said collection vessel and transfer device further including a frangible sealing member for sealing said passage.

* * * * *